United States Patent [19]

Sæbø et al.

[11] Patent Number: 6,015,833
[45] Date of Patent: Jan. 18, 2000

[54] CONJUGATED LINOLEIC ACID COMPOSITIONS

[75] Inventors: Asgeir Sæbø, Oersta, Norway; Carl Skarie, Detroit Lakes, Mich.

[73] Assignee: ConLinCo., Inc., Minn.

[21] Appl. No.: 09/042,767

[22] Filed: Mar. 17, 1998

[51] Int. Cl.$^7$ .................................................. A61K 31/20
[52] U.S. Cl. ............................................. 514/558; 514/560
[58] Field of Search ..................................... 514/558, 560

[56] References Cited

U.S. PATENT DOCUMENTS

| | | | |
|---|---|---|---|
| 2,242,230 | 5/1941 | Burr | 260/405.6 |
| 2,350,583 | 6/1944 | Bradley | 260/405.6 |
| 3,162,658 | 12/1964 | Baltes et al. | 260/405.6 |
| 3,278,567 | 10/1966 | Rathjen et al. | 260/405.6 |
| 3,729,379 | 4/1973 | Emken | 195/30 |
| 4,164,505 | 8/1979 | Krajca | 260/405.6 |
| 4,381,264 | 4/1983 | Struve | 260/405.6 |
| 4,868,001 | 9/1989 | Maruta | 426/623 |
| 5,017,614 | 5/1991 | Pariza et al. | 514/558 |
| 5,070,104 | 12/1991 | Pariza et al. | 514/549 |
| 5,428,072 | 6/1995 | Cook et al. | 514/560 |
| 5,430,066 | 7/1995 | Cook et al. | 514/560 |
| 5,554,646 | 9/1996 | Cook et al. | 514/560 |
| 5,674,901 | 10/1997 | Cook et al. | 514/558 |
| 5,804,210 | 9/1998 | Cook et al. | 424/440 |
| 5,814,663 | 9/1998 | Cook et al. | 514/560 |
| 5,827,885 | 10/1998 | Cook et al. | 514/558 |
| 5,851,572 | 12/1998 | Cook et al. | 426/2 |
| 5,855,917 | 1/1999 | Cook et al. | 424/502 |
| 5,856,149 | 1/1999 | Pariza et al. | 435/134 |

FOREIGN PATENT DOCUMENTS

| | | |
|---|---|---|
| 558881 | of 0000 | United Kingdom . |
| WO97/18320 | 5/1997 | WIPO . |
| WO98/49129 | 11/1998 | WIPO . |

OTHER PUBLICATIONS

Scholfield and Koritalia, "A Simple Method for Preparation of Methyl trans–10,cis–12 Octadecadienoate," *JOACS* 47 (8):303 (1970).

Ron Udell, "Information About Conjugated Linoleic Acid," published by Soft Gel Technologies Incorporated.

Matreya Catalog, 1997, pp. 33–34.

Sugano et al., "Conjugated Linoleic Acid Modulates Tissue Levels of Chemical Mediators and Immunoglobulins in Rats," *Lipids*, 33 5:521–27 (1998).

Selin CLA Product Literature, Jan. 1997.

Hudtwalcker & Co. AS Technical Data Sheet.

Lipid Technology Newsletter, Peter J. Barnes, Ed., vol. 4, No. 5, pp. 85–86 Oct., 1998.

Natural Lipids Ltd. AS Technical Data Sheet, Jan. 20, 1997.

Chin, S. F., W. Liu, J. M. Storkson, Y. L. Ha, M. W. Pariza, "Dietary Sources of Conjugated Dienoic Isomers of Linoleic Acid, a Newly Recognized Class of Anticarcinogens", *J. Food. Comp. Anal.* 5: 185–197 (1992)—published sufficiently before filing date such that the month is not an issue.

Sebedio, J. L., P. Juaneda, G. Dobson, I. Ramilison, J. C. Martin, J. M. Chardigny, W. W. Christie, "Metabolites of Conjugated Isomers of Linoleic Acid (CLA) in the Rat", *Biochem. Biophys. Acta* 1345: 5–10 (1997)—published sufficiently before filing date such that the month is not an issue.

Clement, I., "Review of the Effects of Trans Fatty Acids, Oleic Acid, n–3 Polyunsaturated Fatty Acids, and Conjugated Linoleic Acid on Mammary Carcinogenesis in Animals", *Am. J. Clin. Nutr.* 66 (Suppl.): 1523S–9S (1997)—published sufficiently before filing date such that the month is not an issue.

Sebedio, J. L., A. Grandgirard, and J. Prevost, "Linoleic Acid Isomers in Heat Treated Sunflower Oils", *JAOCS* 65(3): 362–366 (1988)—published sufficiently before filing date such that the month is not an issue.

Holman, R. T., F. Pusch, B. Svingen, H. J. Dutton, "Unusual Isomeric Polyunsaturated Fatty Acids in Liver Phospholipids of Rats Fed Hydrogenated Oil", *PNAS* 88: 4830–34 (1991)—published sufficiently before filing date such that the month is not an issue.

Bradley, T. F., and D. Richardson, "Alkali–Induced Isomerization of Drying Oils and Fatty Acids", *Ind. Eng. Chem.* 34(2): 237–42 (1942)—published sufficiently before filing date such that the month is not an issue.

Radlove, S. B., H. M. Teeter, W. H. Bond, J. C. Cowan, and J. P. Kass, "Catalytic Isomerization of Vegetable Oils", *Ind. Eng. Chem.*, 38(10): 997–1002 (1946)—published sufficiently before filing date such that the month is not an issue.

Cowan, J.C., "Isomerization and Trans–Esterification", *JOACS*, Nov. 1950, p. 492–499 (1950)—published sufficiently before filing date such that the month is not an issue.

Belury, M. A., "Conjugated Dienoic Linoleate: A Polyunsaturated Fatty Acid with Unique Chemoprotective Properties", *Nut. Rev.* 53(4): 83–9 (1995)—published sufficiently before filing date such that month is not an issue.

Park, Y., K. J. Albright, W. Liu, J. M. Storkson, M. E. Cook, M. W. Pariza, "Effect of Conjugated Linoleic Acid on Body Composition in Mice", *Lipids* 32(8): 853–58 (1997)—published sufficiently before filing date such that month is not an issue.

Christie, W. W., G. Dobson, F. D. Gunstone, "Isomers in Commercial Samples of Conjugated Linoleic Acid", *JAOCS* 74 (11): 1231 (1997)—published sufficiently before filing date such that month is not an issue.

Lie Ken Jie, M. S. F., M. K. Pasha, M. S. Alam, "Synthesis and Nuclear Magnetic Resonance Properties of All Geometrical Isomers of Conjugated Linoleic Acids", *Lipids* 32 (10): 1041–44 (1997)—published sufficiently before filing date such that month is not an issue.

(List continued on next page.)

*Primary Examiner*—Kevin E. Weddington
*Attorney, Agent, or Firm*—Medlen & Carroll, LLP

[57] ABSTRACT

Novel compositions containing conjugated linoleic acids are efficacious as animal feed additives and human dietary supplements. Linoleic acid is converted to its conjugated forms in which the resulting composition is low in certain unusual isomers compared to conventional conjugated linoleic products.

16 Claims, 1 Drawing Sheet

OTHER PUBLICATIONS

Sehat, N., M. P. Yurawecz, J. A. G. Roach, M. M. Mossoba, J. K. G. Kramer, Y. Ku, "Silver–Ion High Performance Liquid Chromatographic Separation and Identification of Conjugated Linoleic Acids Isomers", *Lipids* 33 (2): 217–221 (1998)—published sufficiently before filing date such that month is not an issue.

Lie Ken Jie, M. S. F., J. Mustafa, "High–Resolution Nuclear Magnetic Resonance Spectroscopy—Applications to Fatty Acids and Triacylglycerols", *Lipids* 32 (10): 1019–1034 (1997)—published sufficiently before filing date such that month is not an issue.

Willett, W. C., A. Ascherio, "Trans Fatty Acids: Are the Effects Only Marginal?", *Am J Public Health* 84 (5): 722–24 (1994)—published sufficiently before filing date such that month is not an issue.

FIG. 1

CONJUGATED LINOLEIC ACID COMPOSITIONS

FIELD OF THE INVENTION

The present invention relates to the field of human and animal nutrition, and in particular to certain novel compositions of conjugated linoleic acids (CLA). These compositions are prepared according to a novel method that controls isomerization of 9,12-linoleic acid.

BACKGROUND OF THE INVENTION

In 1978, researchers at the University of Wisconsin discovered the identity of a substance contained in cooked beef that appeared to inhibit mutagenesis. The substance was found to be a mixture of positional isomers of linoleic acid (C18:2) having conjugated double bonds. The c9,t11 and t10,c12 isomers are present in greatest abundance, but it is uncertain which isomers are responsible for the biological activity observed. It has been noted from labelled uptake studies that the 9,11 isomer appears to be somewhat preferentially taken up and incorporated into the phospholipid fraction of animal tissues, and to a lesser extent the 10,12 isomer. (See Ha, et al., Cancer Res., 50: 1097 (1991).

The biological activity associated with conjugated linoleic acids (termed CLA) is diverse and complex. At present, very little is known about the mechanisms of action, although several preclinical and clinical studies in progress are likely to shed new light on the physiological and biochemical modes of action. The anticarcinogenic properties of CLA have been well documented. Administration of CLA inhibits rat mammary tumorigenesis, as demonstrated by HA, et al., Cancer Res., 52: 2035s (1992). Ha, et al., Cancer Res., 50: 1097 (1990) reported similar results in a mouse forestomach neoplasia model. CLA has also been identified as a strong cytotoxic agent against target human melanoma, colorectal and breast cancer cells in vitro. A recent major review article confirms the conclusions drawn from individual studies. See Ip, Am. J. Clin. Nutr., 66 (6 Supp): 1523s (1997).

Although the mechanisms of CLA action are still obscure, there is evidence that some component(s) of the immune system may be involved, at least in vivo. U.S. Pat. No. 5,585,400 (Cook, et al.) discloses a method for attenuating allergic reactions in animals mediated by type I or TgE hypersensitivity by administering a diet containing CLA. CLA in concentrations of about 0.1 to 1.0 percent was also shown to be an effective adjuvant in preserving white blood cells. U.S. Pat. No. 5,674,901 (Cook, et al.) disclosed that oral or parenteral administration of CLA in either free acid or salt form resulted in elevation in CD-4 and CD-8 lymphocyte subpopulations associated with cell-mediated immunity. Adverse effects arising from pretreatment with exogenous tumor necrosis factor could be alleviated indirectly by elevation or maintenance of levels of CD-4 and CD-8 cells in animals to which CLA was administered. Finally, U.S. Pat. No. 5,430,066 describes the effect of CLA in preventing weight loss and anorexia by immune stimulation.

Apart from potential therapeutic and pharmacologic applications of CLA as set forth above, there has been much excitement regarding the use of CLA nutritively as a dietary supplement. CLA has been found to exert a profound generalized effect on body composition, in particular redirecting the partitioning of fat and lean tissue mass. U.S. Pat. No. 5,554,646 (Cook, et al.) discloses a method utilizing CLA as a dietary supplement in which pigs, mice, and humans were fed diets containing 0.5 percent CLA. In each species a significant drop in fat content was observed with a concomitant increase in protein mass. It is interesting that in these animals, increasing the fatty acid content of the diet by addition of CLA resulted in no increase in body weight, but was associated with a redistribution of fat and lean within the body. Another dietary phenomenon of interest is the effect of CLA supplementation on feed conversion. U.S. Pat. No. 5,428,072 (Cook, et al.) provided data showing that incorporation of CLA into animal feed (birds and mammals) increased the efficiency of feed conversion leading to greater weight gain in the CLA supplemented animals. The potential beneficial effects of CLA supplementation for food animal growers is apparent.

Another important source of interest in CLA, and one which underscores its early commercial potential, is that it is naturally occurring in foods and feeds consumed by humans and animals alike. In particular, CLA is abundant in products from ruminants. For example, several studies have been conducted in which CLA has been surveyed in various dairy products. Aneja, et al., J. Dairy Sci., 43: 231 (1990) observed that processing of milk into yogurt resulted in a concentration of CLA. Shanta, et al., Food Chem., 47: 257 (1993) showed that a combined increase in processing temperature and addition of whey increased CLA concentration during preparation of processed cheese. In a separate study, Shanta, et al., J. Food Sci., 60: 695 (1995) reported that while processing and storage conditions did not appreciably reduce CLA concentrations, they did not observe any increases. In fact, several studies have indicated that seasonal or interanimal variation can account for as much as three fold differences in CLA content of cows milk. For example, see Parodi, et al., J. Dairy Sci., 60: 1550 (1977). Also dietary factors have been implicated in CLA content variation, as noted by Chin, et al., J. Food Camp. Anal., 5: 185 (1992). Because of this variation in CLA content in natural sources, ingestion of prescribed amounts of various foods will not guarantee that the individual or animal will receive the optimum doses to ensure achieving the desired nutritive effect.

Linoleic acid is an important component of biolipids, and comprises a significant proportion of triglycerides and phospholipids. Linoleic acid is known as an "essential" fatty acid, meaning that the animal must obtain it from exogenous dietary sources since it cannot be autosynthesized. Incorporation of the CLA form of linoleic acid may result in a direct substitution of CLA into lipid positions where unconjugated linoleic would have migrated. But this has not been proven, and some of the highly beneficial but unexplained effects observed may even result from a repositioning of CLA within the lipid architecture at sites where unconjugated linoleic acid would not have otherwise migrated. It is now clear that one source of animal CLA, especially in dairy products, comes from the biochemical action of certain rumen bacteria on native linoleic acid, first isomerizing the linoleic acid to CLA, and then secreting it into the rumen cavity. Kepler, et al., J. Nutrition, 56: 1191 (1966) isolated a rumen bacterium, *Butyrivibrio fibrisolvens*, which catalyzes formation of 9,11-CLA as an intermediate in the biohydrogenation of linoleic acid. Chin, et al., J. Nutrition, 124: 694 (1994) further found that CLA found in the tissues of rodent was associated with bacteria, since corresponding germ-free rats produced no CLA. In the development of a defined commercial source of CLA for both therapeutic and nutritional application, a process for generating large amounts of defined material is needed. The problem with most CLA products made by conventional approaches is their heterogeneity, and substantial variation in isoform from batch to batch. Considerable attention has been given to the fact that the ingestion of large amounts of hydrogenated oils and shortenings, instead of animal tallow, has resulted in a diet high in trans-fatty acid content. For example, Holman, et al., PNAS, 88:4830 (1991) showed that rats fed hydrogenated oils gave rise to an accumulation in rat liver of unusual polyunsaturated fatty acid isomers, which appeared to interfere with the normal metabolism of naturally occurring polyunsaturated fatty acids. These concerns were summarized in an early Editorial in Am. J. Public Health, 84: 722 (1974). Therefore, there exists a strong need for a CLA biologically active product of defined composition.

SUMMARY OF THE INVENTION

The present invention provides a novel compositions of isomerized fatty acids derived from clarified food grade seed oils. The linoleic acid contained in a seed oil selected as having at least 50 percent linoleic acid, as a practical matter, is typically in excess of 90 percent the 9,12-octadecadienoic isomer. During isomerization, the 9,12-octadecadienoic acid is converted to a mixture of other isomers to form a composition having at least 50 percent CLA.

The conjugated linoleic acid-containing composition is intended for consumption by both humans and animals, including food animals such as cattle, swine, sheep, and birds, and as a human medicament and a nutritional supplement. It is an important object of this invention to provide a safe, defined product for these applications. Also, conventional products contain significant quantities of unknown fatty acid species and unusual isomers resulting from processing. Among the unusual CLA isomers are the 11,13-octadecadienoic acid and 8,10-octadecadienoic acid isomers.

In the present composition, a high percentage of linoleic acid is converted primarily to the conjugated c9,t11 and t10,c12 isomers in a carefully controlled reaction yielding greater than 90 percent of these isomers, so that less than a combined 1 percent of the 11,13 isomers, less than 1 percent of the 8,10 isomers, less than 1 percent of the double trans species (the t9,t11 and t10,t12 isomers), and less than 1 percent total unidentified linoleic acid species is present in contrast to conventional compositions. In many individual product runs, the final composition has levels of these species virtually undetectable by GC analysis. The 1 percent limit in concentration of the 11,13 and 8,10 isomers serves as a convenient and practical quality assurance standard of purity for a commercial scale manufactured food grade product.

The present invention also provides a new process for making novel conjugated linoleic acid-containing compositions of the requisite purity and defined composition. The process comprises the steps of dissolving in the specific non-aqueous solvent propylene glycol, an alkali compatible with a non-aqueous medium such as potassium hydroxide, cesium hydroxide, cesium carbonate, or an organic alkali such as tetraethyl ammonium hydroxide, in the absence of metallic-based isomerization catalyst systems, blending into the alkaline propylene glycol a seed oil, heating under an inert gas atmosphere and at ambient pressures to a temperature in the range of 130–165 degrees C., preferably about 150 degrees C. under nonreflux conditions, separating the fatty acid fraction by acidification, and optionally further purifying and dehydrating by vacuum molecular distillation and/or centrifugation. Optionally, the process stream may be interrupted after the reaction mix is prepared, either prior to or after the heat step. The mix may then be stored for further processing in continuous acidification and distillation steps and/or be further processed at another location. After heating to effect isomerization, the isomerized blended reaction mix contains 30–60 percent processed seed oil, 10–40 percent alkali, and 30–60 percent propylene glycol. In this process it is important to utilize propylene glycol because of its heating properties and the patterns of isomerization obtained. The components of the dissolved fatty acid reaction mix are present, as follows:

30–60 percent seed oil

10–40 percent alkali

30–60 percent propylene glycol

Thus, in the preferred method embodiment, the process comprises forming a blended reaction mix containing linoleic acid-containing seed oil, propylene glycol, and an alkali compatible with a nonaqueous medium, isomerizing said linoleic acid contained in said seed oil by heating to form conjugated linoleic acids, aquefying to release glycerol. Toxicity is avoided, as will be posed if other, undesirable organic solvents such as ethylene glycol are used. Under the nonreflux conditions, it is possible to vary the processing temperature over a range to obtain the desired result with oils of differing fatty acid composition. The temperature is critical, as the percentage of trans,trans species, as well as other undesired and unidentified species increases as temperature rises. The processing time requires about 2 to 6.5 hours and gives isomerized yields of greater than 90 percent, frequently as high as 99.5 percent.

In the present process, use of sunflower and safflower oil is preferred because of its high native 9,12 linoleic acid content, but also because of low levels of sterols, contaminating phospholipids, and other residues that tend to foul the processing equipment and result in a less pure final product. Other seed oils, such as corn, soybean, and linseed oils, may also be employed, but the final product will be less compositionally defined, and the impurity levels may stray to close to the threshold values for quality control contemplated above, and the isomerization process itself will be less predictable. While a seed oil containing at least 50 percent linoleic acid is desirable as a practical matter for industrial isomerization, so as to optimize yields per processing unit, there is no process limitation in starting with linoleic acid-containing materials having less or greater linoleic content. Lesser linoleic content may occur as in the situation in which oils from different sources are blended, or where oils are combined with nonoil components prior to isomerization. Similarly, the linoleic acid content of the isomerization fluid can be much higher than the levels present in native seed oils, as in the situation in which purified or synthetic linoleic is to be isomerized.

DETAILED DESCRIPTION OF THE PREFERRED EMBODIMENT

The composition of the present invention results from a highly controlled isomerization process, and from using the preferred starting material of sunflower or safflower oil. This composition has not heretofore been obtained, for application to an industrial scale, because the conventional processes historically produce conjugated linoleic acids for entirely different purposes, namely, as drying oils in the paint industry. Also, there has not been an appreciation of the implications of the isomer content of the final product, because the analytical methods for characterizing the fatty acids has not been widely available.

In the older isomerization processes, some of which are still in use in more modern format, production of the conjugated fatty acids was carried out in aqueous alkali (generally NaOH) at high temperatures in excess of 200 degrees C. and usually at superatmospheric pressures. For example, U.S. Pat. No. 2,350,583 (Bradley) discloses an aqueous alkali process utilizing treated soaps in which both conjugation and polymerization occurred under rather harsh conditions at 200 to 250 degrees C. for a period of several hours. The fractions of drying oil, starting with linseed oil, were obtained by distillation. See also Br. Patent No. 558,881 for a very similar process. In a variation of the process, U.S. Pat. No. 4,381,264 teaches a process where a low water content reaction zone (0.5% water) contains stoichiometric base in the presence of $SO_2$ to obtain conjugation of the double bonds of various polyunsaturated fatty acids. The aqueous alkali process was adapted in U.S. Pat. No. 4,164,505 to a continuous flow process in which an alkali metal hydroxide and water are continuously charged in a flow zone maintained at between 200 and 370 degrees C. At these temperatures, the time of reaction should be greatly foreshortened, but there is relatively little control over the isomerization. At the higher end of the temperature range, one would predict almost complete conversion to double trans species.

Methods of producing CLA using various nonaqueous solvents and catalysts have been described in the literature. Burr (U.S. Pat. No. 2,242,230) discloses the use of solvents such as methanol, butanol, ethanol and glycol in combination with various catalysts. These reaction parameters are summarized in Table 1. With the exception of glycol, the reactions were conducted either under reflux conditions or in sealed tubes. These reaction conditions result in imprecise control of two of the important reactions parameters identified by the Inventors—temperature and pressure. Imprecise control of these reactions parameters is likely to lead to less than complete conjugation and the formation of undesirable isomers.

TABLE 1

U.S. Pat. No. 2,242,230

| Solvent | Catalyst | Temperature | Time |
| --- | --- | --- | --- |
| Ethanol | KOH, NaOH | reflux or higher* | varied |
| Butanol | KOH, NaOH | reflux or higher* | varied |
| Glycol | KOH | 195° C. | varied |
| Isoamyl Alcohol | KOH | reflux or higher* | varied |
| Butanol | Tributyl-amine | 140–175° C. | 22 hours |
| Butanol | Potassium Acetate | 175° C. | 36 hours |
| Butanol | Trisodium Phosphate | 175° C. | 36 hours |
| Butanol | Potassium Phosphate | 175° C. | 36 hours |
| Butanol | Sodium Benzoate | 175° C. | 36 hours |
| Butanol | Potassium Thiocyanate | 175° C. | 36 hours |
| Butanol | Borax | 175° C. | 36 hours |

Likewise, Baltes et al., (U.S. Pat. No. 3,162,658) disclose the use of nonaqueous solvents and various metallic bases as catalysts for the conjugation of fatty acids. The various reaction parameters of the methods described by Baltes et al. are summarized in Table 2. Baltes et al. also disclose the use various low boiling point solvents. As most of these reactions were conducted at temperatures above the boiling point of the solvent employed, it is apparent that the reactions were conducted under pressure, which is an independent factor influencing the formation of octadecadienoic acid isomers. The product derived from these reactions will thus contain undesirable isomers.

TABLE 2

U.S. Pat. No. 3,162,658

| Solvent | Catalyst | Temperature | Time |
| --- | --- | --- | --- |
| Methanol | KOH | 60–140° C. | variable |
| Methanol | Potassium Methylate | 140° C. | variable |
| Butanol | Potassium Methylate | 140° C. | variable |
| Ethanol | Potassium Methylate | 140° C. | variable |
| Isopropanol | Potassium Methylate | 120–140° C. | variable |
| Heptane/ 3° Butanol | Potassium Butylate | reflux | variable |
| 3° Butanol | Cesium Butylate | 140° C. | variable |
| Ethylene Diamine | Potassium Methylate | 140–160° C. | variable |
| Methanol | Sodium Amide | 140° C. | variable |

The CLA of the present invention lacks isomers such as the 8,10 isomer, the 11,13 isomer, and the various trans-trans isomers. This composition was produced by a tightly controlled nonaqueous alkali isomerization process presented in flow diagram form in FIG. 1. Preferably, sunflower oil or safflower oil are reacted at an ambient pressure under an inert gas atmosphere with an excess of alkali in a high-boiling point solvent, namely propylene glycol at a temperature below the boiling point of the solvent. These reaction conditions allow for precise control of the temperature (and constant ambient pressure) of the conjugation process. Preferably the alkali is an inorganic alkali such as potassium hydroxide, cesium hydroxide, cesium carbonate or an organic alkali such as tetraethyl ammonium hydroxide. The catalyst is preferably provided in a molar excess as compared to the fatty acid content of oil. The solvent is propylene glycol. Preferably, the reaction is conducted within a temperature range 130 to 165° C., most preferably at about 150° C. The time of the reaction may vary, however, there is an increased likelihood of the formation of undesirable isomers when the reaction is conducted for long periods of time. A relatively short reaction time of 2.0 to 6.5 hours has proved satisfactory for excellent yields.

It will be understood to a person skilled in the art that to produce the desired composition, the reaction conditions described above may be varied depending upon the oil to be conjugated, the source of alkali and equipment. Preanalysis of a particular oil may indicate that the conditions must be varied to obtain the desired composition. Therefore, the temperature range, pressure, and other reaction parameters represent a starting point for design of the individual process and are intended as a guide only. For example, it is not implied that the described temperature range is the only range which may be used. The essential aspect is to provide precise temperature control. However, care must be taken because increasing the pressure may lead to less than complete isomerization and the formation of undesirable isomers. Finally, the length of the conjugation reaction may be varied. Generally, increasing amounts of undesirable isomers are formed with increasing length. Therefore, the optimal reaction time allows the reaction to go nearly or essentially to completion but does not result in the formation of undesirable isomers.

Figure 1:
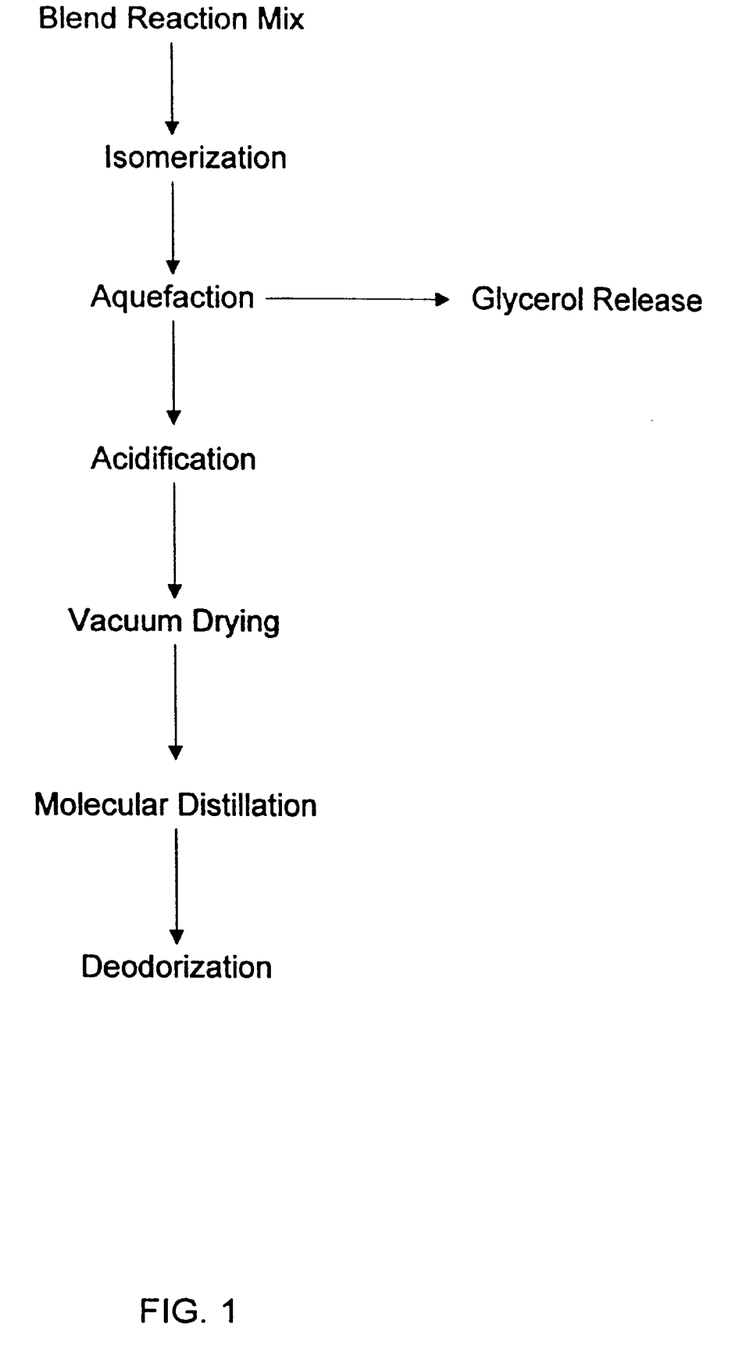
FIG. 1 is a flow diagram of the procedure used to produce CLA.

Following the conjugation reaction, the resulting CLA containing composition may be further purified according to FIG. 1. To separate the fatty acids form the conjugation reaction mix, the reaction mix is cooled to approximately 95° C., an excess of water at 50° C. is added, and the mixture slowly stirred while the temperature is reduced to about 50° C. to 60° C. Upon addition of the water, a soap of the fatty acids is formed and glycerol is formed as a by-product. Next, a molar excess of concentrated HCl is added while stirring. The aqueous and nonaqueous layers are then allowed to separate at about 80–90° C. The bottom layer containing water and propylene glycol is then drawn off. The remaining propylene glycol is removed by vacuum dehydration at 60–80° C.

The dried CLA composition may then preferably be degassed in degassing unit with a cold trap to remove any residual propylene glycol. Next, the CLA is distilled at 190° C. in a molecular distillation plant at a vacuum of 10-1 to 10-2 millibar. The advantage of this purification system is the short time (less than one minute) at which the CLA is held at an elevated temperature. Conventional batch distillation procedures are to be strictly avoided since they involve an elevated temperature of approximately 180–200° C. for up to several hours. At these elevated temperatures the formation of undesirable trans-trans isomers will occur. Approximately 90% of the feed material is recovered as a slightly yellow distillate. The CLA may then be deodorized by heating to about 120–170° C., preferably at about 150° C. for 2 hours to improve smell and taste. Excessive heat may result in the formation of trans-trans isomers. These procedures produce a CLA composition with a solvent level of less than about 5 ppm, preferably less than about 1 ppm. This process eliminates toxic trace levels of solvent so that the resulting composition is essentially free of toxic solvent residues.

The processes described above are readily adaptable to both pilot and commercial scales. For example, 400 kg of safflower oil may be conjugated at 150° C. for 5 hours in 400 kg of propylene glycol with 200 kg KOH added as a catalyst. The resulting CLA may then be purified as described above. Further, commercial scale batch systems may be easily modified to produce the desired CLA composition. For example, stainless steel reactors should be preferably glass lined to prevent corrosion due to pH levels of below 3.0. However, it should be noted that conjugation processes utilizing nonaqueous solvents are generally less corrosive than this conducted with water.

The preferred oils for conjugation are sunflower and safflower oil. As compared to soybean oil, these oils have lower concentrations of undesirable components such as phosphatides and sterols. These undesirable components may contribute to the formation of gums which foul the conjugation equipment and other undesirable polymers. Various properties of these oils are summarized in Tables 3, 4, and 5.

TABLE 3

COMPARISON OF CONTAMINANTS
Phosphatides

| Soybean | 1.5–3.0% |
|---|---|
| Sunflower | .4–1% |
| Sunflower | .4–1% |

TABLE 4

Sterols (unsaponifiables by percent)

| Soybean | | Sunflower | | Sunflower | |
|---|---|---|---|---|---|
| Campesterol | 20* | Campesterol | 8 | Campesterol | 13 |
| Stigmasterol | 20 | Stigmasterol | 8 | Stigmasterol | 9 |
| β-Sitosterol | 53 | β-Sitosterol | 60 | β-Sitosterol | 52 |
| $\Delta^5$ Avensterol | 3 | $\Delta^5$ Avensterol | 4 | $\Delta^5$ Avensterol | 1 |
| $\Delta^7$ Stigmasterol | 3 | $\Delta^7$ Stigmasterol | 15 | $\Delta^7$ Stigmasterol | 15 |
| $\Delta^7$ Avenasterol | 1 | Avenasterol | 4 | Avenasterol | 3 |

Percentage of 0.36 percent total Total *May not equal 100
0.36% total in oil    0.36%    0.36%

TABLE 5

| | Soybean | Sunflower | Sunflower |
|---|---|---|---|
| Iodine Value | 134.6 | 135.4 | 143.6 |
| Saponification value | 190.7 | 190.6 | 190.3 |
| Unsaponification value | .6 | .7 | .6 |

In the Examples that follow, several comparative experiments were carried out to highlight the key properties of the present CLA compositions in contrast to those made under either suboptimal conditions or in accordance with the aqueous alkali methods of the prior art. In Example 1, the CLA was prepared by the present method. CLA was produced by the conventional aqueous alkali method in Example 2. In Example 3, the reaction of Example 1 is substantially repeated, only at high temperature. Finally, in Example 4, the aqueous alkali reaction substantially identical to that of Example 2 is run at low temperature. The precise conditions and details of each experiments are set forth in the Examples. The profiles of the analysis of the CLA isomer content are set forth in tables 1–4.

Referring to the data in Table 5, the relative area percentage is given for each identified peak corresponding to the individual isomers, for each of the four experiments. The GC plot gave a number of peaks for each sample tested. The area under each of these peaks was integrated to obtain a total value. The identity of the peak was determined by its relative position, from published atlases of standard elution profiles, and the scientific literature. The top row represents the residual value for unconjugated starting material, 9,12-linoleic acid. Both low and high temperature reaction in propylene glycol gave extremely high conversions of over 99 percent of the total starting material.

Referring to column 1, it is strikingly apparent that unlike any of the control compositions, in Example 1, a peak corresponding to 11,13 mixture of isomers, the peak corresponding to c11,c13 specifically, the peaks for any of the 8,10 isomers, and the peak for unidentified isomers are all entirely missing. In the case of c9,t11 isomer, the peaks in GC for both the 8,10 and 9,11 isomers are superimposed, and are here resolved only for Example 1 material by subtracting out that portion of the peak identified as 8,10 by NMR studies. This was not done in the other experiments, so that the row 3 gives the values for combined 8,10 and 9,11 for Examples 2–4. In general, for the 8,10, 11,13, and unidentified isomers, a value of less than 1 percent down to undetectable is of therapeutic and nutritional value, because it reduces to trace levels potentially deleterious contaminants, especially those known to have suspect absorption pathways in lipogenesis. In non-ruminants, for example, addition of 0.25 to 2.5 percent CLA to the diet can increase the incidence of CLA in tissues to approximate that in ruminants, so that other animals can be a source of CLA provided adulterating isomers are not present.

Example 2 provides a typical aqueous alkali product representative of conventionally manufactured CLAs. Conversion is less efficient both overall, and in producing the c9,t11 and t10,c12 isomers. Note also a high percentage of the suspect 11,13 isomers, and a significant percentage of unidentified material.

Example 3 illustrates the criticality of the temperature parameter. An upward shift in temperature in propylene glycol media sharply increases the amount of the contaminating isomers at the expense of the c9,t11 and t10,c12 isomers. Also of interest, at the higher temperature there is a dramatic increase in the trans, trans species, as double bond rearrangements are favored which yield a more stable electron configuration at levels of increased energy stress.

Example 4 illustrates that decreasing the temperature in the aqueous alkali system, in fact, reduces the amounts of some of the contaminating isomers. However, there is a dramatic drop in yield, and the level of the 11,13 group of isomers remains very high, suggesting that the formation of this electron configuration is influenced more by the action of base in an aqueous medium, than is explained by overall kinetic energy in the system. Note also the extremely long reaction time of 22.5 hours; too long for an efficient industrial scale batch process.

Table 6 merely converts the relative isomer percentages in the various reactions as a function of peak area to their corresponding peak ratios. The present process produces a virtually complete conversion of 9,12-linoleic acid to an approximate equal amount of each of the two desired CLA isomers. At the higher temperature, even in propylene glycol, the incidence of the 11,13 isomer is still less one third that of the low temperature aqueous alkali process.

EXAMPLE 1

Isomerization of Safflower Oil Using Propylene Glycol at Low Temperature

Safflower oil was isomerized in propylene glycol at low temperatures using KOH as a catalyst. The isomerization apparatus consisted of a two-necked flask with a thermometer placed in one neck, leaving a small opening to release excess pressure. A nitrogen supply was attached to the other neck of the flask. Solutions added to the flask were agitated by the use of a magnetic bar and a magnetic stirrer. The temperature of the flask was controlled by placing the flask in a thermostat-controlled oil bath placed on the magnetic stirrer.

The flask was filled with 60.27 g propylene glycol and 28.20 g KOH and immersed into the oil bath. The temperature was increased to 130° C. to dissolve the KOH. After the KOH had dissolved, 60.09 g of safflower oil was introduced into the flask. A high volume of nitrogen was circulated through the two-neck flask for 5 min. and then reduced to a lower volume. The mixture was heated to 150° C., which took approximately 40 min. The mixture was then allowed to react at 150° C. for 3.5 hours. At intervals, 3 ml samples were withdrawn for analysis.

The samples were placed directly into 6 ml of hot water and citric acid was added in excess until the free fatty acids separated out as the top layer. Heating was necessary to prevent solidification while the citric acid was added. To convert the free fatty acids into methylesters for analysis by Gas Chromatography, 0.025 g of the free fatty acids, 5 ml of a 4% solution of HCl and ethanol were added to a test tube. Nitrogen was added to the tube, then the tube was sealed and placed in a water bath at 60° C. for 20 min. The tube was then cooled and 1 ml purified water and 5 ml isooctane were added. Nitrogen was added to the tube and the tube was shaken for 30 seconds. The resulting upper layer was added to 1 μl of purified water in a new test tube and again shaken under nitrogen. The resulting upper layer was then washed of isooctane and decanted into a third test tube. A small amount of sodium sulfate was added for water absorption. A 1 μl sample was then injected directly into the Gas chromatograph.

The gas chromatography conditions were as follows:
System: Perkins-Elder Auto System
Injector: Splitless at 240° C.
Detector: Flame Ionization Detector at 280° C.
Carrier: Helium
Column: WCOT Fused Silica 0.25 mm×100 M, CP-SL 88 for FAME, DF 0.2
Oven Program: 80° C. (0 min.) increasing to 220° C. at 10° C. per min. and held at 220° C. for 10 min.

All results are expressed as the relative peak area percentage. Standards are generally unavailable, so the peaks which eluted were verified with other systems. GC-MS determines the number, but not the position of cis and trans bonds. Therefore, NMR analysis was used to verify the bond positions. The main peaks were c9,t11 and t10,c12. For NMR analysis of CLA isomers, please see Marcel S. F. Lie Ken Jie and J. Mustafa, Lipids, 32 (10) 1019–34 (1997), incorporated herein by reference.

This data, presented in Table 6 and summarized in Table 10, demonstrates that isomerization of safflower oil using polypropylene glycol as a solvent, KOH as a catalyst, and low temperatures results in the production of conjugated linoleic acid lacking 8,10 and 11,13 isomers. The highly polar columns utilized in this experiment may be successfully used to separate the 8,10 and 11,13 isomers from c9,t11 and t10,c12 isomers. The 8,10 isomers tend to coelute or elute just after the c9,t11 isomer. The 11,13 isomer elutes in front of the t10,c11 isomer or coelutes with the t10,c12 isomer, depending on the column conditions.

The conjugated linoleic acid produced according to this method by characterized by comparing the various isomers produced. First, the isomerization reaction went essentially to completion. The completeness of the reaction is obtained by dividing the total peak area the for linoleic acid isomers minus residual c9, t12 linoleic acid by the total peak area. This value is 0.994. Second, the ratio of c9,t11 and t10,c12 isomers to total peak area may be determined. This value is 0.953. Third, the ratio of the t9,t11 and t10,t12 isomers to the c9,t11 and t10,c12 isomers may be determined. This value is 0.010. Fourth, the ratio of the t9,t11 and t10,t12 isomers to total peak area may be determined. This value is 0.009. Fifth, the ratio of the t10,c12 isomer to the c9,t11 isomer may be determined. This value is 1.018. These ratios are summarized in Table 11.

EXAMPLE 2

Aqueous isomerization at high temperature and pressure

Fifty grams of water and 25.32 g NaOH were added to a high pressure reactor (Parr Model 450 ML Benchtop Alloy 400, equipped with a pressure gauge and stirrer.) The NaOH was allowed to dissolve and 94.0 g safflower oil was added to the reactor. The reactor was closed and flushed for 2 min. with nitrogen and then all valves were closed. The reactor was heated in an electrical gasket to 210° C. and maintained at that temperature for 6 hours. The temperature was then reduced to 60° C. before pressure was released and the reactor opened. Two grams of the resulting solidified soap were taken from the reactor and dissolved in water at approximately 40° C. Citric acid was then added to reduce the pH of the solution to below 6. A sample was withdrawn from the fatty acid top layer and prepared for Gas Chromatography as in Example 1.

The results of the gas chromatography are presented in Table 7 and summarized in Table 10. These data indicate that this isomerization method results in the formation of relatively high amounts of the 8,10 and 11,13 isomers. Ratios are presented in Table 11.

EXAMPLE 3

Non-aqueous Alkali Isomerization of Safflower Oil at High Temperature and Pressure 100.48 g propylene glycol and 46.75 g of KOH were added to a high-pressure reactor as described in Example 2. The reactor was then heated to 130° C. to dissolve the KOH. 100.12 g of safflower oil were then added to the KOH-propylene glycol mixture. The reactor was closed, flushed for 1 min. with nitrogen, and all valves closed. The reactor was then heated to 210° C. and maintained at that temperature for 1 hour. The reactor was cooled and the contents decanted into 120 g of hot water. While stirring, 35.3 g 37% HCl and 27.59 g citric acid were serially added to the fatty acids. A sample was taken from the top layer and dried in a vacuum flask at 60° C. A sample of the resulting fatty acids was analyzed by gas chromatography as described in Example 1.

The results are presented in Table 8 and summarized in Table 10. This experiment demonstrates that isomerization of safflower oil with KOH and a non-aqueous solvent at high temperature results in the formation of significant amounts of 8,10 and 11,13 isomers, as well as t9,t11 and t10,t12 isomers. Ratios are presented in Table 11.

EXAMPLE 4

Aqueous alkali reaction at low temperature 49.94 g water and 39.96 g NaOH were added to a high-pressure reactor as described in Example 3. This mixture was heated until the NaOH dissolved. Next, 100.54 g of safflower oil was added to the high-pressure reactor, the reactor was flushed with nitrogen, and all valves closed. The high-pressure reactor was heated to 179° C. for 22.5 hours. Samples were prepared for Gas Chromatography as in Example 3. The data is provided in Table 9 and summarized in Table 10. This experiment demonstrates that when low temperatures are used for aqueous alkali isomerization, the conjugation reaction does not go to completion. Furthermore, significant amounts of the 8,10 and 11,13 isomers are produced. Ratios are presented in Table 11.

TABLE 6

| Peak # | Time (Min) | Component Name | Area (%) | Area ($\mu V \cdot s$) | Height ($\mu V$) |
|---|---|---|---|---|---|
| 1 | 38.164 | | 0.08 | 4101.65 | 622.28 |
| 2 | 49.539 | C16:0 | 6.29 | 335897.80 | 32745.95 |
| 3 | 53.107 | C16:1 | 0.06 | 3240.60 | 447.82 |
| 4 | 61.620 | C18:0 | 2.38 | 127182.30 | 12999.14 |
| 5 | 64.821 | C18:1 c9 | 12.34 | 659111.72 | 52209.40 |
| 6 | 65.254 | | 0.57 | 30402.68 | 3475.09 |
| 7 | 67.263 | | 0.11 | 5757.35 | 758.08 |
| 8 | 67.940 | | 0.10 | 5523.00 | 700.44 |
| 9 | 68.755 | | 0.24 | 12816.90 | 1543.27 |
| 10 | 69.310 | | 0.22 | 11803.80 | 1430.59 |
| 11 | 69.846 | C18:2 c9,c12 | 0.44 | 23336.75 | 2500.24 |
| 12 | 73.618 | | 0.28 | 14828.70 | 1838.66 |
| 13 | 76.621 | | 0.16 | 8400.65 | 1050.19 |
| 14 | 77.388 | CLA c9,t11 | 36.51 | 1950669.98 | 124313.83 |
| 15 | 78.370 | CLA t10,c12 | 37.16 | 1985488.96 | 132265.33 |
| 16 | 78.664 | CLA c9,c11 | 1.06 | 56583.10 | 5699.43 |
| 17 | 78.880 | CLA c10,c12 | 1.26 | 67503.55 | 4572.65 |
| 18 | 80.102 | CLA t9,t11/ t10,t12 | 0.73 | 39110.00 | 4743.28 |
| 19 | 85.165 | | 0.03 | 1621.65 | 231.32 |
| | | | 100.00 | 5343381.15 | 384147.01 |

TABLE 7

| Peak # | Time (Min) | Component Name | Area (%) | Area ($\mu V \cdot s$) | Height ($\mu V$) |
|---|---|---|---|---|---|
| 1 | 36.554 | | 0.09 | 4122.05 | 627.02 |
| 2 | 47.785 | C16:0 | 6.68 | 290571.30 | 28224.34 |
| 3 | 51.280 | C16:1 | 0.07 | 3188.05 | 425.57 |
| 4 | 59.787 | C18:0 | 2.63 | 114362.95 | 12678.63 |
| 5 | 62.923 | C18:1 c9 | 13.12 | 570712.08 | 42259.71 |
| 6 | 63.346 | | 0.72 | 31329.22 | 3774.35 |
| 7 | 65.355 | | 0.54 | 23620.70 | 2848.31 |
| 8 | 66.034 | | 0.67 | 28980.78 | 3333.95 |
| 9 | 66.574 | | 0.10 | 4370.91 | 594.22 |
| 10 | 66.811 | | 0.35 | 15045.61 | 1469.30 |
| 11 | 67.352 | | 0.41 | 18002.20 | 2035.53 |
| 12 | 67.889 | C18:2 c9,c12 | 1.43 | 62002.15 | 6714.22 |
| 13 | 69.200 | | 0.09 | 3840.85 | 474.10 |
| | | | | | 474.10 |
| 14 | 71.680 | | 0.30 | 13099.10 | 1744.21 |
| 15 | 74.640 | | 1.62 | 70689.87 | 4117.23 |
| 16 | 75.310 | CLA c9,t11/ 8,10 | 24.87 | 1082087.96 | 57619.24 |
| 17 | 76.032 | CLA 11,13 | 14.72 | 640440.14 | 42975.86 |
| 18 | 76.277 | CLA t10,c12 | 16.00 | 695923.85 | 63512.81 |
| 19 | 76.450 | CLA c8,c10 | 1.26 | 54676.10 | 7614.29 |
| 20 | 76.626 | CLA c9,c11 | 2.08 | 90411.44 | 10891.36 |
| 21 | 76.881 | CLA c10,c12 | 3.00 | 130593.96 | 11727.80 |
| 22 | 77.022 | CLA c11,c13 | 1.77 | 77065.69 | 9906.74 |
| 23 | 77.477 | | 0.66 | 28867.85 | 3322.69 |
| 24 | 77.868 | | 0.63 | 27391.94 | 2934.68 |
| 25 | 78.173 | CLA t9,t11/ t10, t12 | 6.00 | 260985.40 | 26124.10 |
| 26 | 83.140 | | 0.12 | 5164.40 | 586.21 |
| 27 | 85.878 | | 0.06 | 2735.80 | 347.01 |
| | | | 100.00 | 4350282.35 | 348883.46 |

TABLE 8

| Peak # | Time (Min) | Component Name | Area (%) | Area ($\mu V \cdot s$) | Height ($\mu V$) |
|---|---|---|---|---|---|
| 1 | 38.249 | | 0.08 | 3999.70 | 599.26 |
| 2 | 49.639 | C16:0 | 6.41 | 333807.80 | 32279.13 |

TABLE 8-continued

| Peak # | Time (Min) | Component Name | Area (%) | Area (μV · s) | Height (μV) |
|---|---|---|---|---|---|
| 3 | 53.218 | C16:1 | 0.06 | 3123.00 | 427.39 |
| 4 | 55.508 | | 0.03 | 1322.20 | 190.60 |
| 5 | 61.753 | C18:0 | 2.55 | 132854.50 | 14939.09 |
| 6 | 64.104 | C18:1 c9 | 0.03 | 1640.30 | 245.73 |
| 7 | 64.950 | | 12.92 | 672672.91 | 53345.47 |
| 8 | 65.382 | | 0.64 | 33297.29 | 3728.28 |
| 9 | 65.783 | | 0.03 | 1411.20 | 219.76 |
| 10 | 67.403 | | 0.62 | 32194.66 | 2836.09 |
| 11 | 67.793 | | 0.24 | 12660.05 | 1495.10 |
| 12 | 68.088 | | 0.68 | 35371.43 | 3210.82 |
| 13 | 68.421 | | 0.07 | 3684.10 | 473.77 |
| 14 | 68.635 | | 0.04 | 1948.63 | 257.65 |
| 15 | 68.890 | | 0.29 | 14979.18 | 1499.63 |
| 16 | 69.192 | | 0.04 | 2268.69 | 324.39 |
| 17 | 69.430 | | 0.25 | 13028.21 | 1369.93 |
| 18 | 69.947 | C18:2 c9,c12 | 0.23 | 11895.70 | 1125.77 |
| 19 | 70.341 | | 0.02 | 1168.20 | 196.75 |
| 20 | 73.741 | | 0.31 | 15930.60 | 1965.82 |
| 21 | 75.448 | | 0.08 | 3906.00 | 387.98 |
| 22 | 76.768 | | 1.79 | 93172.74 | 6637.34 |
| 23 | 77.002 | | 0.63 | 32882.76 | 5024.06 |
| 24 | 77.389 | CLA c9,t11/ 8,10 | 15.62 | 813447.45 | 57234.62 |
| 25 | 77.735 | | 1.92 | 99754.50 | 8641.88 |
| 26 | 78.045 | CLA 11,13 | 4.03 | 209728.35 | 19826.20 |
| 27 | 78.335 | CLA t10,c12 | 12.63 | 657681.44 | 62016.93 |
| 28 | 78.566 | CLA c8,c10 | 0.64 | 33432.80 | 5277.06 |
| 29 | 78.727 | CLA c9,c11 | 2.21 | 114935.49 | 10791.54 |
| 30 | 79.079 | CLA c10,c12 | 3.98 | 207339.28 | 12766.61 |
| 31 | 79.663 | CLA c11,c13 | 1.40 | 73036.34 | 6275.58 |
| 32 | 80.516 | CLA t9,t11/ t10,t12 | 29.39 | 1529956.09 | 100323.85 |
| 33 | 82.318 | | 0.03 | 1563.70 | 230.42 |
| 34 | 85.289 | | 0.07 | 3657.50 | 423.53 |
| 35 | 88.093 | | 0.05 | 2368.50 | 301.03 |
| | | | 100.00 | 5206121.30 | 416889.05 |

TABLE 9

| Peak # | Time (Min) | Component Name | Area (%) | Area (μV · s) | Height (μV) |
|---|---|---|---|---|---|
| 1 | 38.154 | | 0.09 | 3371.70 | 501.86 |
| 2 | 49.501 | C16:0 | 6.80 | 253221.00 | 25807.11 |
| 3 | 53.100 | C16:1 | 0.07 | 2723.55 | 353.01 |
| 4 | 55.391 | | 0.03 | 1078.10 | 142.65 |
| 5 | 61.618 | C18:0 | 2.68 | 100015.20 | 11002.94 |
| 6 | 63.990 | | 0.03 | 946.40 | 156.50 |
| 7 | 64.791 | C18:1 c9 | 13.13 | 489016.55 | 38313.02 |
| 8 | 65.270 | | 0.69 | 25645.55 | 2670.46 |
| 9 | 67.296 | | 0.12 | 4466.65 | 558.35 |
| 10 | 67.960 | | 0.11 | 4012.70 | 517.76 |
| 11 | 68.800 | | 0.37 | 13840.49 | 1314.91 |
| 12 | 69.370 | | 0.30 | 11141.11 | 1245.85 |
| 13 | 70.001 | C18:2 c9,c12 | 20.52 | 764287.35 | 62474.1031 9.72 |
| 14 | 73.538 | | 0.30 | 11075.20 | 1357.19 |
| 15 | 76.519 | | 0.42 | 15662.14 | 1154.22 |
| 16 | 77.231 | CLA c9,t11/ 8,10 | 22.45 | 836230.58 | 56972.76 |
| 17 | 77.911 | CLA 11,13 | 7.56 | 281633.54 | 24467.27 |
| 18 | 78.197 | CLA t10,c12 | 19.77 | 736384.86 | 66688.46 |
| 19 | 78.559 | CLA c8,c10 | 1.21 | 45158.40 | 3837.29 |
| 20 | 78.787 | CLA c9,c11 | 0.87 | 32564.06 | 3409.07 |
| 21 | 78.953 | CLA c10,c12 | 0.89 | 33053.57 | 2499.70 |
| 22 | 79.413 | CLA c11,c13 | 0.12 | 4453.10 | 353.06 |
| 23 | 79.792 | | 0.13 | 4936.60 | 436.59 |
| 24 | 80.052 | CLA | 1.13 | 42203.55 | 4550.59 |

TABLE 9-continued

| Peak # | Time (Min) | Component Name | Area (%) | Area (μV · s) | Height (μV) |
|---|---|---|---|---|---|
| | | t9,t11/ t10, t12 | | | |
| 25 | 82.298 | | 0.03 | 981.60 | 150.46 |
| 26 | 82.946 | | 0.03 | 1107.95 | 151.48 |
| 27 | 85.135 | | 0.10 | 3639.90 | 383.36 |
| 28 | 87.927 | | 0.06 | 2212.50 | 254.61 |
| | | | 100.00 | 3725063.90 | 311570.23 |

TABLE 10

Relative Area Percentage

| Isomer | Example 1 | Example 2 | Example 3 | Example 4 |
|---|---|---|---|---|
| c9,t12 | 0.44 | 1.43 | 0.23 | 20.52 |
| c9,t11 | 36.51 | na | na | na |
| c9,t11/ 8,10 | <0.5* | 24.87 | 15.62 | 22.45 |
| t10,c12 | 37.16 | 16.00 | 12.63 | 19.77 |
| c9,c11 | 1.06 | 2.08 | 2.21 | 0.87 |
| c8,c10 | <0.5 | 1.26 | 0.64 | 1.21 |
| c10,c12 | 1.26 | 3.00 | 3.98 | 0.89 |
| t9,t11/ t10,t12 | 0.73 | 6.00 | 29.39 | 1.13 |
| 11,13 | <0.5 | 10.23 | 4.05 | 7.65 |
| c11,c13 | <0.5 | 1.77 | 1.40 | 0.12 |
| Unidentified | <0.5 | 2.91 | 4.34 | 0.55 |
| CLA Total | 76.88 | 72.61 | 74.24 | 54.55 |
| Total area | 77.32 | 74.04 | 74.47 | 75.07 |

*total percentage of 8,10 is less than 0.5
na-value is reflected as component of c9,t11/8,10

TABLE 11

| Isomer Ratio | | Example 1 | Example 2 | Example 3 | Example 4 |
|---|---|---|---|---|---|
| Total CLA isomer | Total peak area | 0.994 | 0.981 | 0.997 | 0.727 |
| c9,t11-t10,c12 | Total peak area | 0.953 | 0.552* | 0.379* | 0.562* |
| t9,t11-t10,t12 | c9,t12-t10,c12 | 0.010 | 0.147* | 1.040* | 0.027* |
| t9,t11-t10,t12 | Total peak area | 0.009 | 0.081 | 0.395 | 0.015 |
| Total 11,13 | Total peak area | na | 0.223 | 0.073 | 0.102 |
| t10,c12 | c9,t11 | 1.018 | 1.554* | 0.809* | 0.881* |

*c9,t11 includes 8,10 isomer
na-no 11,13 detected

What is claimed is:

1. An isomerized linoleic acid composition containing at least 50 percent conjugated linoleic acid
   said isomerized linoleic acid composition being characterized in having less than 1 percent of a class of octadecadienoic acid isomers selected from 11,13-octadecadienoic acid isomers, 8,10-octadecadienoic acid isomers and trans-trans octadecadienoic acid isomers.

2. The composition of claim 1 wherein said composition contains less than 1 percent total 11,13-octadecadienoic acid isomers and trans-trans octadecadienoic acid isomers.

3. The composition of claim 1 wherein said composition contains less than 1 percent total 8,10-octadecadienoic acid isomers and trans-trans octadecadienoic acid isomers.

4. The conjugated linoleic acid-containing composition of claim 1 wherein said composition has a total t9,t11-octadecadienoic acid and t10,t12-octadecadienoic acid level of less than 1 percent.

5. The linoleic acid-containing composition of claims 1–4 wherein said composition is an isomerized commodity seed oil.

6. The linoleic acid-containing composition of claim 5 wherein said commodity seed oil is selected from the group consisting of sunflower oil and safflower oil.

7. The composition of claim 1, wherein said conjugated linoleic acid is an ester.

8. The composition of claim 7, wherein said ester is a methylester.

9. A food product comprising:
   isomerized conjugated linoleic acid, said isomerized conjugated linoleic acid being characterized in having less than 1 percent of a non-naturally occurring class of octadecadienoic acid isomers.

10. The food product of claim 9, wherein said food product contains less than 1% total 11,13-octadecadienoic acid isomers and trans-trans isomers.

11. The food product of claim 9, wherein said food product contains less than 1% total 8,10-octadecadienoic acid isomers and trans-trans octadecadienoic acid isomers.

12. A food supplement comprising:
   isomerized conjugated linoleic acid, said isomerized conjugated linoleic acid being characterized in having less than 1 percent of a class of octadecadienoic acid isomers selected from 11,13-octadecadienoic acid isomers, 8,10-octadecadienoic acid isomers and trans-trans octadecadienoic acid isomers.

13. The food supplement of claim 12, wherein said food supplement contains less than 1% total 11,13-octadecadienoic acid isomers and trans-trans isomers.

14. The food supplement of claim 12, wherein said food supplement contains less than 1% total 8,10-octadecadienoic acid isomers and trans-trans octadecadienoic acid isomers.

15. The food supplement of claim 12, wherein said food supplement is for use in animals.

16. The food supplement of claim 12, wherein said food supplement is for use in humans.

* * * * *